(12) United States Patent
Mullender et al.

(10) Patent No.: US 6,418,806 B1
(45) Date of Patent: Jul. 16, 2002

(54) MODEL TEST APPARATUS AND METHOD

(75) Inventors: Andrew J Mullender; Brian A Handley; Michael H Coney, all of Derby; Peter T Ireland; Andrew Neely, both of Oxford, all of (GB)

(73) Assignee: Rolls-Royce plc, London (GB)

( * ) Notice: Subject to any disclaimer, the term of this patent is extended or adjusted under 35 U.S.C. 154(b) by 0 days.

(21) Appl. No.: 09/433,953

(22) Filed: Nov. 4, 1999

(30) Foreign Application Priority Data

Nov. 23, 1998 (GB) ............................................ 9825624

(51) Int. Cl.$^7$ ............................................... G01K 11/16
(52) U.S. Cl. ...................................................... 73/866.4
(58) Field of Search ............................. 73/865.6, 866.4; 374/210

(56) References Cited

U.S. PATENT DOCUMENTS 4,885,633 A   12/1989   Buck

FOREIGN PATENT DOCUMENTS

| EP | 0707203 A | 4/1996 |
|----|-----------|--------|
| GB | 2217011 A | 10/1989 |
| GB | 2284261 A | 5/1995 |

*Primary Examiner*—Robert Raevis
(74) *Attorney, Agent, or Firm*—W. Warren Taltavull; Manelli Denison & Selter PLLC

(57) ABSTRACT

The fire resistance of components normally subject to a standard flame test is evaluated using low temperature model tests. Reynolds number, Froude number, the pressure ratio of the flame to the surrounding atmosphere are matched in the modelling parameters and account is taken of the Prandtl number. Also, the model flow is controlled so as to match the change of momentum flux ratio in the flow through the burner used in a standard flame test. The method allows testing of easily produced model components at temperatures less than 90° C., with savings of cost and time.

Figure 1:
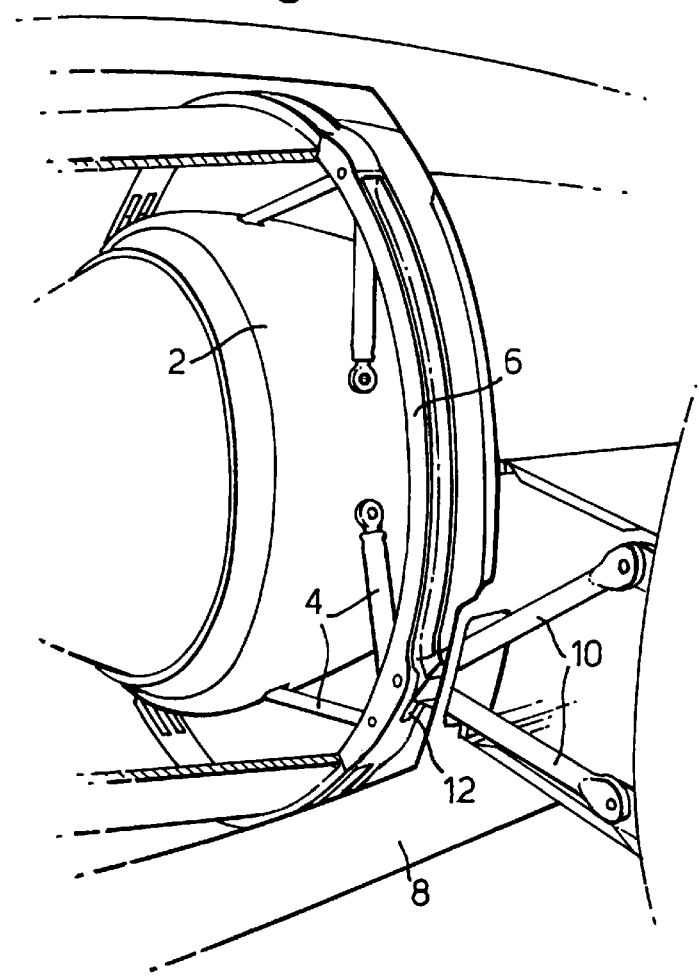

11 Claims, 4 Drawing Sheets

MODEL TEST APPARATUS AND METHOD

This invention relates to the evaluation of the fire resistance of components, in particular for air worthiness compliance of components in and around aircraft engines, although it can be applicable to fire resistance evaluations for other purposes.

Air worthiness regulations require the testing of critical components to ensure that fire in and around aircraft engines does not hazard aircraft safety. In the tests, e.g. as set out in ISO 2685, the components are subjected to flame attack from a standard flame, to evaluate an in-service fire event. An array of thermocouples are mounted on the surface of the component and the maximum temperatures recorded from the test are used to determine the viability of the component during a fire event. This can be by reference to induced thermal stresses or degradation of the material, e.g. deformation, oxidation or melting.

Testing costs are significant. At the same time, however, the accuracy of the analysis is limited by the spatial resolution of the metal temperatures that can be provided by the thermocouple array. The process is also expensive and time-consuming, particularly if a component initially fails the test and must be redesigned. This can lead to overdesign of a component due to excessive caution, with resulting cost and weight penalties.

The present invention it concerned with the development of a modelling system which allows fire resistance tests to be performed more rapidly and more economically. It is also concerned with the provision of a low-temperature heating device that can simulate the designated flame source of a standard test technique.

It is already known to model simulated high temperature conditions on aero-engine components using Perspex models with thermochromic liquid crystals on their surfaces, the models being immersed in a relative low temperature (less than 90° C.) airstream to map the heat transfer coefficients across the surface of the model by observing colour changes in the liquid crystal. This technique (described, for example, in "*Full surface local heat transfer coefficient measurements in an integrally cast impingement cooling geometry*", Gillespie et al (1996), *ASME* 96-GT-200) has been used to determine external and internal heat transfer coefficients in turbine blades.

According to one aspect of the present invention, a method is provided for evaluating the resistance of a component to a fire in which a scale model of the component is provided with a thermochromic liquid crystal on its surface and is subjected to a gas flow at an elevated temperature closer to ambient than to a hydrocarbon flame temperature, the gas density, flow rate and the scale of the model being chosen to at least substantially match the Reynolds number and Froude number of the flow over the component in the fire test conditions, and to at least substantially match the ratio of flame density to the density of the ambient surrounding in fire test conditions, and the reaction of said liquid crystal is recorded when subjected to the gas flow.

To allow the method to be performed in free air conditions, preferably the gas flow contains at least a substantial portion of a gas lighter than air. In particular, it may contain helium as a major component.

It is also desirable, to improve simulation of the flame plume of the standard flame, to ensure that the gas flow reproduces the ratio of momentum flux of the standard flame combustion products to total reactant momentum flow in the entry to the standard burner.

According to another aspect of the invention, a flame simulation device for use in low temperature simulation of a standard flame of a fire resistance test, comprising respective sources of pressure air and helium and means for producing a mixed flow therefrom in predetermined proportions and heating said flow, a duct for receiving said flow and simulating a standard test burner, said duct having an exit face formed by a plate with a series of apertures for the passage of the heated mixed gases, said apertures having an area in relation to the area of the duct downstream of the plate which produces a change of momentum flux in said flow substantially reproducing the ratio of the momentum flux of the standard flame combustion products to the momentum flux of the reactants on entry to the standard burner.

Figure 2A:
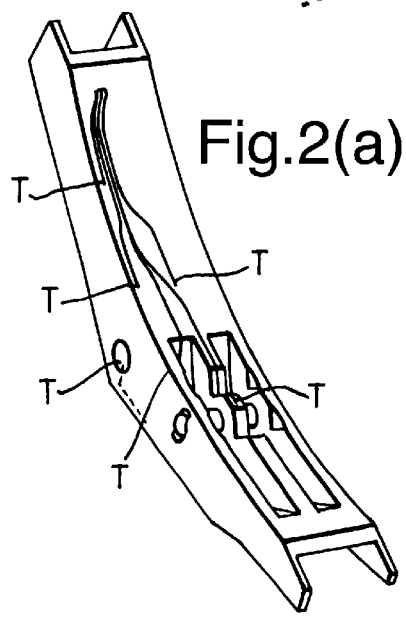
Figure 2B:
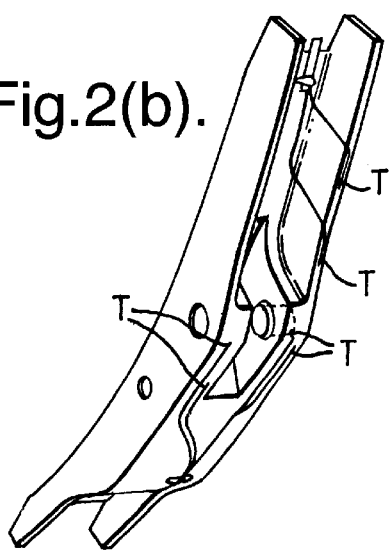
Figure 3:
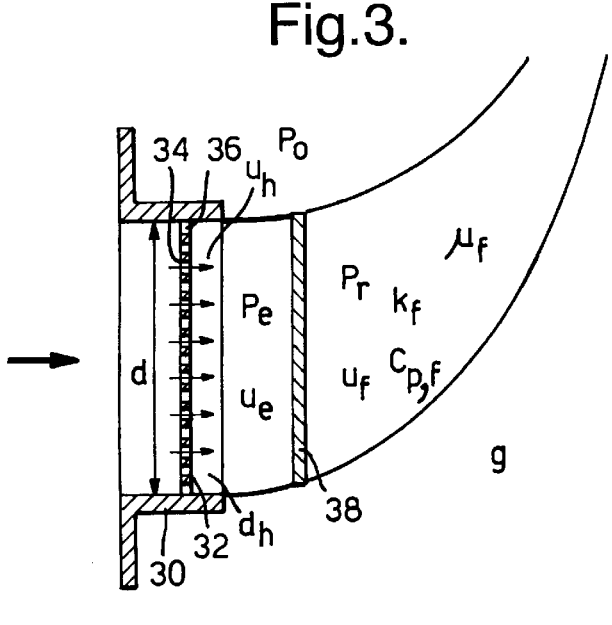
Figure 4:
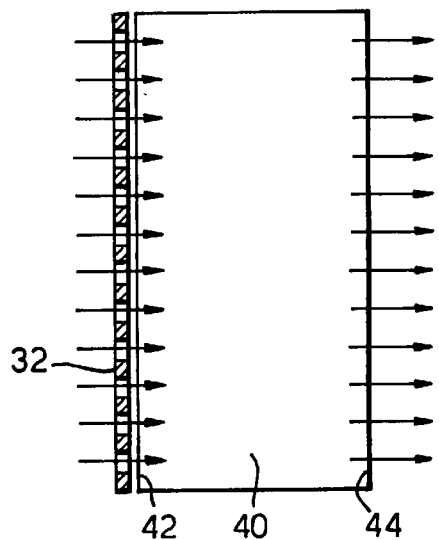
Figure 5:
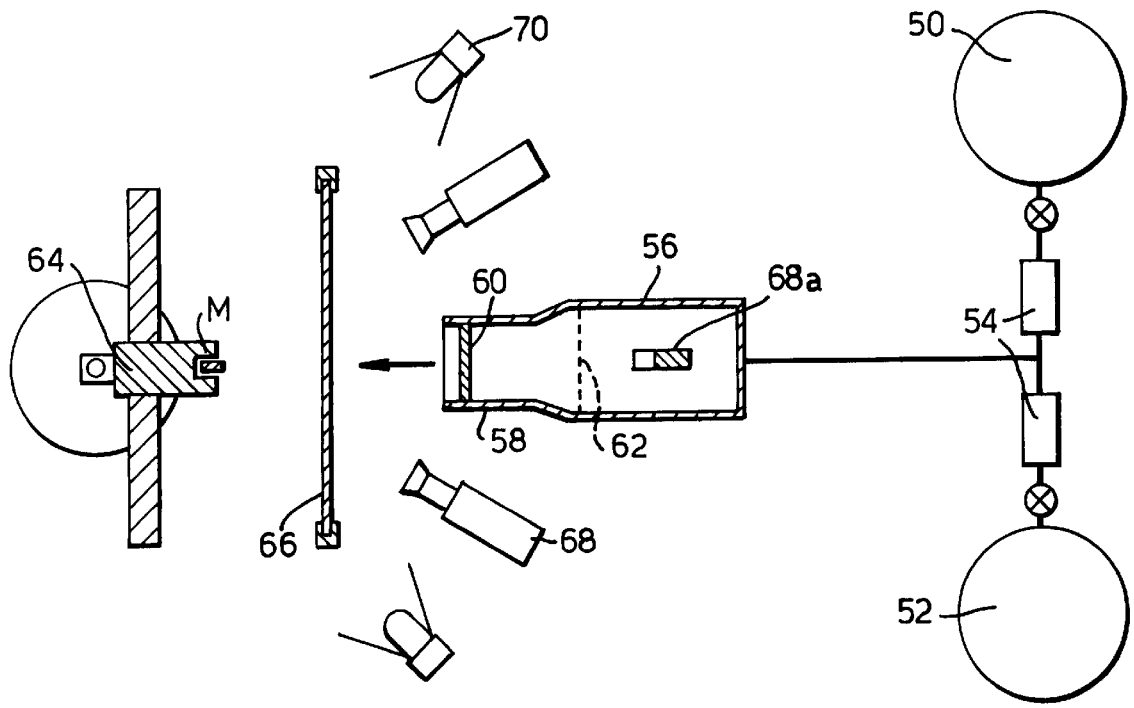
Figure 6:
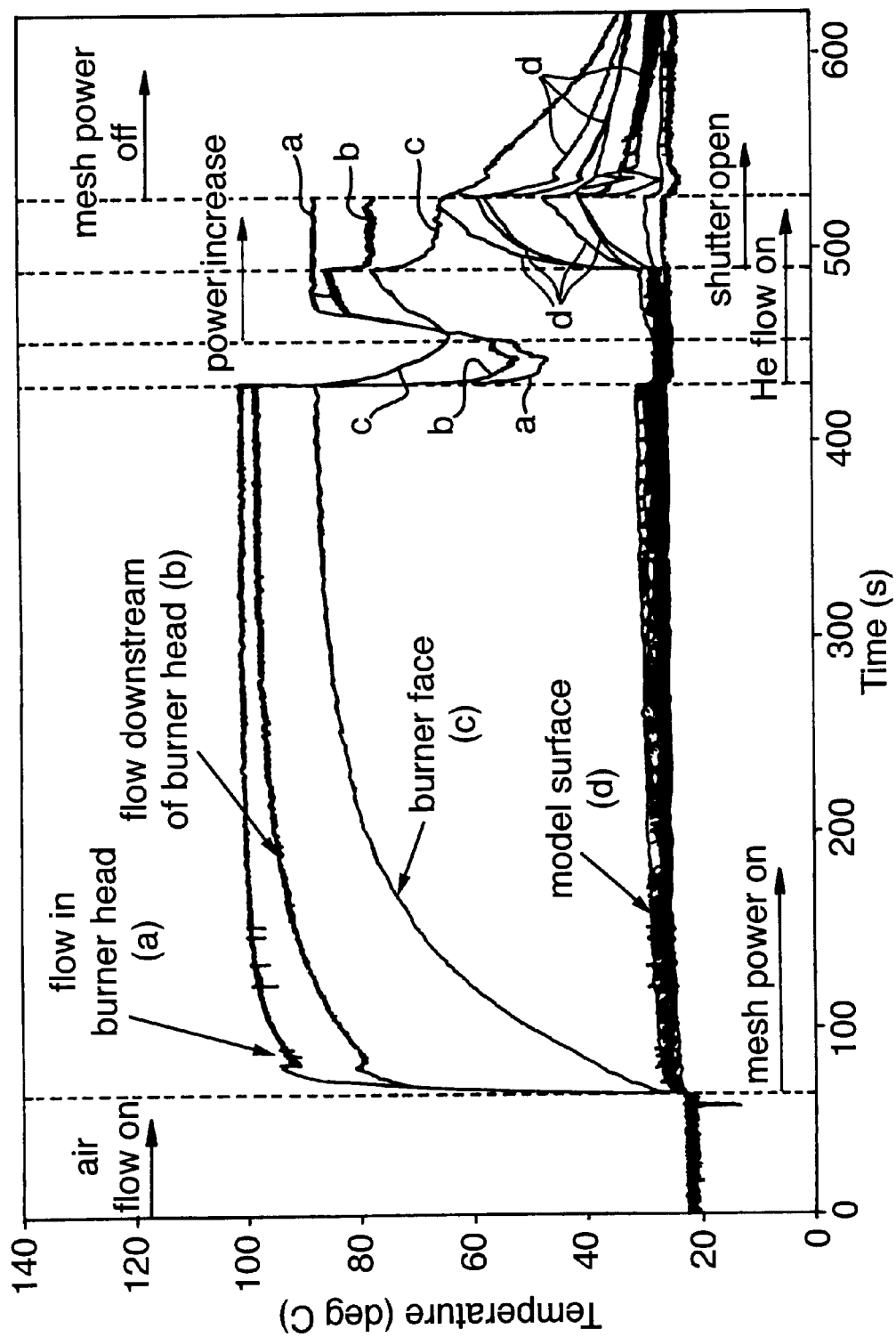
Figure 7:
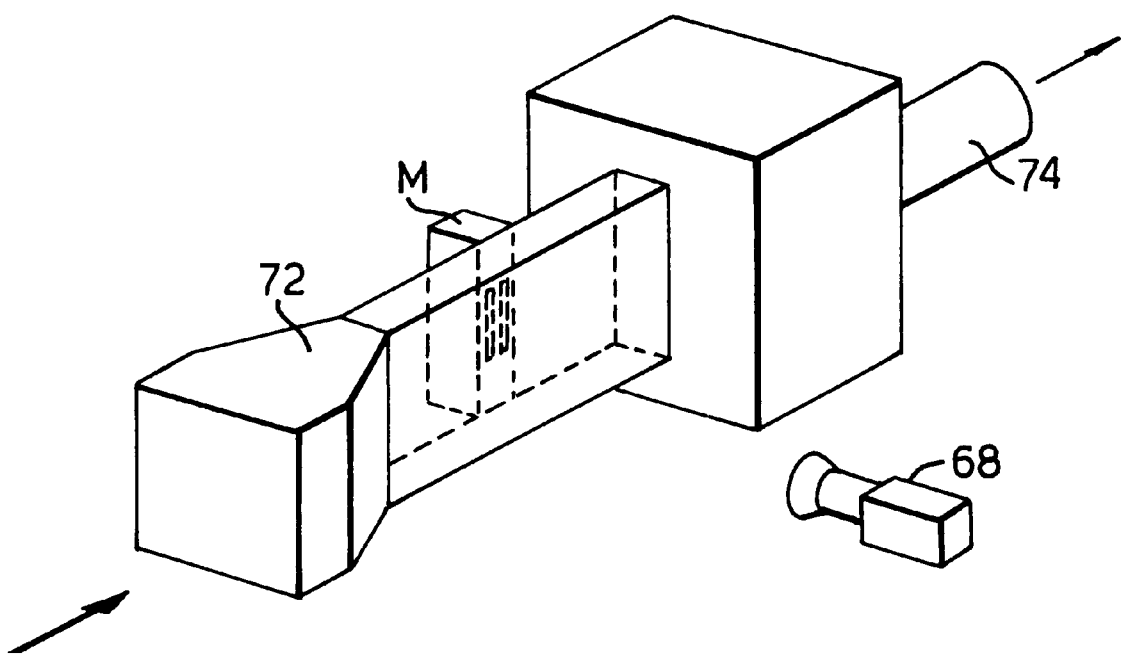

The invention will now be further described with reference to the accompanying drawings, in which:

FIG. 1 is a fragmentary illustration of a fusilage mounted turbofan engine, showing the rear mount support system, FIGS. 2*a* and 2*b* are oblique views of a part of the rear mount support ring in FIG. 1, FIG. 3 is a schematic side view of a standard burner of the kind prescribed in ISO 2685, FIG. 4 is a diagram illustrating the change of momentum flux in the flow from a standard burner, FIG. 5 is a schematic plan view of the apparatus for modelling the heat transfer coefficients of a test component, FIG. 6 is a chart of temperature-time profiles at a series of locations on the apparatus and test model of FIG. 5 during a test run, and FIG. 7 is a schematic illustration of a modification of the apparatus of FIG. 5 for measurements in rear cavities of the test model.

FIG. 1 illustrates a typical aircraft jet engine rear mount support structure for a small fuselage-mounted turbo-fan.

The rear cone fairing 2 of the engine is shown connected by A-frames to a rear mount support ring 6 within the nacelle 8 of the engine. Struts 10 extend into the nacelle from the airframe to attach to a mounting lug 12 on the support ring as the sole rear mounting point of the engine. It is required that the support ring 6 be shown to be able to support the structural engine loads without catastrophic failure in fire conditions. The support ring is thus an example of a component which fire tests according to ISO 2685 are required. FIGS. 2(*a*) and (*b*) show typical temperature measurement locations T on a portion of the rear mount support ring at which thermocouples are attached for such a test.

The current testing procedure presumes not only that the design of the component has been finalised, but also that production tooling has been made available. Apart from the costs of the tests, therefore, if the component fails there can be serious consequences in terms of delay and cost. These could be avoided if a model test procedure was available that could be performed on an easily produced model that could be made available even before finalisation of the design, and that permitted testing at lower temperatures without exposure to a burner flame.

In the standard burner shown in FIG. 3, a cylindrical burner head 30 has a front plate 32 provided with a first set of holes 34 receiving pipes (not shown) through which propane is supplied, and a further set of holes 36 through which air flows. Combustion between the fuel and air occurs in a zone 38 downstream of the plate and the flame plume extends upwards from the combustion zone.

To model the combustion flow, in a low temperature analogue of the standard burner flame, it is required to simulate the distribution of heat transfer coefficients from the flame. A number of dimensionless groups should be matched in the simulation. Thus, the convective heat transfer in the combustion products dictates that the Reynolds number (Re) must be conserved to achieve dynamic similarity for flows with viscous forces acting. With the diameter d of the burner head as the leading dimension, $$Re_d = \frac{\rho u d}{\mu}$$

As the significant differences in temperature between the standard burner flame and the low temperature analogue will result in variation of the thermodynamic properties of the fluid, attention must be paid to the Prandtl number (Pr) which relates the relative thicknesses of the hydrodynamic and thermal boundary layers.

$$Pr = \frac{\mu c_p}{k}$$

However, the variation that will occur in the Prandtl number between the standard burner flame and the low temperature analogue is small and can be accounted for in the subsequent scaling of the modelled heat transfer coefficient data.

The significant difference in densities between the flow and the surroundings introduces buoyancy as an important parameter. Conservation of the Froude number (Fr) will permit dynamic similarity of flows with gravity forces acting.

$$Fr - \frac{u}{\sqrt{gd}}$$

Essentially, conservation of the Froude number achieves matching of the ratio of inertia to gravity forces acting on the jet exiting the burner head.

As the model flow velocity can be easily adjusted, it is possible to obtain a new dimensionless parameter by combining Red and Fr, and eliminating u $$Re \cdot \frac{1}{Fr} = \frac{\rho d^{3/2} g^{1/2}}{\mu}$$

Thus, the required scale factor for matching Red and Fr is defined by $$\frac{d_1}{d_2} = \frac{\rho_1 \mu_2^{2/3}}{\rho_1 \mu_2}$$

It is also required, if there is to be a rigorous analogy between the standard flame and the low temperature analogue, in which the distribution of heat transfer coefficients from the standard flame burner are simulated in the lower temperature conditions of the model, the model flow should at least approximately reproduce the shape and behaviour of the standard flame. It is found, however, that matching of the dimensionless groups already referred to is not sufficient to give this result.

Thus, the spreading of the flame and its mixing with the surroundings will be governed by the relative magnitude of the flame density ($p_f$) to that of its ambient surroundings ($p_o$) Thus, the simulation should conserve the density ratio $$\text{density ratio} = \frac{\rho_o}{\rho_f}$$

Considering also the flow through the standard burner, the inlet flow is formed as a series of jets, from the propane delivery pipes and from the air inlet holes respectively. The fuel thus burns in discrete jets and the combustion products mix with the dilution air until the flows are mixed out. The flow over the path from the exit of the jets from the apertured plate 32 to the mixed out state can be represented as a control volume 40, shown as a constant cross-section in FIG. 4. From the inlet face 42 to the outlet face 44 of the control volume there will be a change of momentum flux from two different causes.

Firstly, the flow area through the plate is less than the flow area further downstream in the control volume. The associated decrease in velocity, assuming the outer boundary of the flow has a substantially uniform cross-sectional area, decreases the momentum flux.

Secondly, the increase in temperature caused by combustion reduces the density of the flow, and there is also a change in density associated with the changed chemistry of the combustion products. For a given flow cross-sectional area, therefore, the velocity increases and so does the momentum flux.

Because the combustion zone is not surrounded by a constant pressure, a change in momentum flux can be balanced by a difference in pressure across the indicated control volume. This pressure difference occurring across a flame front has been termed the flame thrust. If it is assumed that the flow field and shape of the zone of the flow under study is governed only by the momentum fluxes at entry to and exit from the control volume, a further dimensionless group thus enters into consideration, namely the ratio of momentum flux. That is to say, the effect of flame thrust can be simulated by matching the momentum flux ratio of the model flow to momentum flux ratio of the standard flame between entry to the burner and the mixed out state.

Considering the nature of the entry flow through the holes in the burner face plate, then for a given mass flow rate the momentum flux is a function of the hole diameter d and the number of holes n. That is to say, the total momentum flux at the hole exits, which equals the product of the mass flow rate ($m_h$) and flow velocity ($u_h$) through the holes is $$4 \frac{m^2}{n \rho \pi d^2}$$

The combination of the two parameters n and d is effectively the porosity of the face plate as the diameter of the plate is already specified. The positioning of the holes will also influence the shape of the plume, but as individual jets of sufficiently small diameter will quickly coalesce into a single larger plume, it is sufficient to simply reproduce the overall plume diameter.

After combustion has occurred in the standard burner there is a change in momentum flux from the exit of the burner to the plume due to both a decrease in momentum flux through the expansion of the individual jet flows out to the plume diameter and an increase in momentum flux due to the reduction in density of the flow through combustion of the fuel-air mixture. Observation indicates that it can be assumed that the expansion of the combustion gas only increases the velocity and does not increase the cross-section of the burner plume.

The momentum flux can therefore be scaled by conserving the ratio of the momentum fluxes of the upstream and downstream flows. If the low temperature model flow does not require combustion, the two pre-combustion and combustion influences on the momentum flux as described above can be simulated jointly by a single series of holes in the model burner face plate, if the porosity is suitably adjusted. That is to say, the ratio of the area of the apertures to the area of the duct downstream of the apertures (or, more strictly, the area occupied by the flow when the aperture jets mix out) is controlled to scale the momentum flux ratio.

FIG. 5 illustrates the test rig for the simulated flame test of a model component applying the principles discussed above. Perspex was chosen as a suitable material for the model of the rear mount support ring, having well defined properties. As Perspex is usable for an extended period only at temperatures below 90° C., a gas temperature of 80° C. was selected for the simulated flame flow. In order to achieve the required density ratio at such a low temperature, if air were used for the simulated flame, the test rig would have to be immersed in a higher density atmosphere. To avoid that inconvenience, a reduced density simulated flow was produced so that it was not necessary to adjust the density of the surroundings. In the testing described here, a mixture of 96% helium and 4% air was used for the simulated gas flow.

Matching of Re was achieved by reducing the model flow velocity at scale. Substitution of appropriate viscosities gave a scale factor of 0.48, but this was rounded to 0.5 to simplify the fabrication of the test rig and model. The flow properties and simulation parameters for a range of gases and different scales are set out in the following table:

as the model burner. When the mesh heating was switched on (t=60), temperature within the burner quick rose but the model surface was virtually unaffected because it was shielded by the shutter. When the burner temperature had equilibrated (t=420) the helium flow was started to produce the 96:4 helium air mixture. The gas flow rate was then increased to the test velocity and after a short final equilibration the shutter was opened (t=490) and observations of the liquid crystal changes were made over a period of 40 seconds, before the mesh heating and the gas flow were stopped. The observations recorded in the video cameras were analysed to obtain the heat transfer coefficients of the model. This data was then used to predict the rear mount support ring temperatures in a standard flame test using a finite element software program (which can be any of a number of commercially available program for heat transfer analysis) with scaled values of the heat transfer coefficients measured on the model used as thermal boundary conditions in the finite element analysis.

For the relatively brief period of each test, one dimensional semi-infinite heat transfer could be assumed in the analysis. Thus, at any time, the contours of recorded change in the liquid crystal on the model surface, which were themselves isotherms, represented contours of constant heat transfer coefficients. At any point on the model surface, the local heat transfer coefficient h was thus a function only of the driving temperature difference $(T_g-T_i)$, the crystal change temperature $(T_c)$, the material properties of the substrate (pck) and the time (t) at which the contour appeared.

| | Re | density ratio $\frac{\rho_o}{\rho_f}$ | Fr | scale | density (kg · m$^{-3}$) | viscosity (N · s · m$^{-2}$) | velocity (m · s$^{-1}$) | mass flow (kg · s$^{-1}$) |
|---|---|---|---|---|---|---|---|---|
| standard flame @ 1907° C. | 5077 | 7.50 | 0.655 | 1 | 0.16 | 6.46e-5 | 2.05 | 0.0082 |
| air @ 80° C. | 5077 | 1.20 | 0.034 | 1 | 1.00 | 2.09e-5 | 0.11 | 0.0026 |
| Helium @ 80° C. | 5077 | 8.57 | 0.259 | 1 | 0.14 | 2.24e-5 | 0.81 | 0.0028 |
| 4% air + Helium @ 80° C. | 5077 | 7.50 | 0.227 | 1 | 0.16 | 2.24e-5 | 0.71 | 0.0028 |
| 4% air + 96% Helium @ 80° C. | 5077 | 7.50 | 0.642 | 0.5 | 0.16 | 2.24e-5 | 1.42 | 0.0014 |

As FIG. 5 shows, flows from air and helium sources, 50,52 regulated by meters 54, were fed to a heating chamber 56 forming an exit duct 58 at the exit face of which is a perforated plate 60 which scaled the porosity the standard flame burner as already described. Within the chamber a fast response mesh heater 62 was able to heat the air-helium mixture before it reached the exit plate. The heated gas flow was directed onto a half scale Perspex model μ of the test component, to the surface of which a thermochromic liquid crystal had been applied, mounted on a support 64 in front of the plate. A shutter 66 was able to screen the model initially from the flow while the plate temperature is being equilibrated. Video cameras 68 trained on the model were located at each side of the chamber and a further video camera 68a viewed the model directly from the chamber, for which the purpose the perforated plate was of a transparent material such as polycarbonate. Lighting 70 was provided, as appropriate, to illuminate the model for the cameras.

The test procedure followed is shown in FIG. 6. At the start (t=0) only air was driven through the chamber 56 acting $$h = \frac{\beta \sqrt{\rho c k}}{\sqrt{t}}$$

in which:

$$\frac{T_c - T_i}{T_g - T_i} = 1 - \exp(\beta^2) \operatorname{erfc}(\beta)$$

The semi-infinite one-dimensional behaviour of the substrate assumed for this equation is valid for most of the surface of the model because the test periods were considerably less than 60 seconds. In regions where the model was heated from opposite surfaces, such as the web, care was required in reducing the data for such regions only in the initial part of the test as the time over which semi-infinite one dimensional behaviour could be assumed is shortened.

For longer times, the surface temperature data can be reduced using thick plate models.

There are also regions where three-dimensional effects occur, but these are confined to the immediate zones of edges of the model and have no significant effect on the analysis.

In the core of the simulated flame playing on the model, the adiabatic wall temperature equals the gas temperature $T_g$ which is nominally uniform, but at the edges of the flame the hot gas mixes with the surrounding air, reducing $T_g$. To correctly calculate the local heat transfer coefficient h, the distribution of adiabatic wall temperature across the surface of the model must be determined. This can be done by applying a second thermochromic liquid crystal with a different transition temperature $T_c$ to the model. The two equations formed can be solved simultaneously at any point for the two unknown $T_g$ and h.

The degree of mixing between the surrounding air and the heated gas plume in the model is approximately the same as for the standard flame, since the fluid dynamics have been matched, but the temperature in the mixed region will not be correct as the procedure does not reproduce the temperature and specific heat ratios $$\frac{T_{plume}}{T_o} \text{ and } \frac{C_{p,plume}}{C_{p,o}}$$

The temperature of the mixed region ($T_{mix}$) is governed by the enthalpy of the mixture, as calculated from the mass fractions by $$H_{mix} = H_{plume} \cdot M_{plume} + H_0 \cdot M_0$$

Thus $$Tm = \frac{C_{p,f,Tf} \cdot T_f \cdot M_f + C_{p,o,To} T_o \cdot M_o}{C_{p,f,Tm} \cdot M_f + C_{p,o,Tm} \cdot M_o}$$

This in fact the adiabatic wall temperature and here the values of specific heat are evaluated at the local mixture temperature. As the variation of $C_p$ with temperature is small the iteration required to arrive at a solution is minimal. The unknown mass fractions can be determined from the low temperature experiment given that $$M_o + M_f = 1$$

The equation for Tm can thus be rearranged to allow the direct calculation of the two mass fractions $$M_o = \frac{C_{p,f,T_f} \cdot T_f + C_{p,f,T_m} \cdot T_m}{T_m(C_{p,o,T_m} - C_{p,f,T_m}) - C_{p,o,T_o} \cdot T_o + C_{p,f,T_f} \cdot T_f}$$

The specific heat of the mixture can then be determined from $$C_{p,mix} = C_{p,plume} \cdot M_{plume} + C_{p,o} \cdot M_o$$

When the h levels are scaled to the flame condition, using the approach described below, the local flame temperatures to be applied as the boundary conditions can be determined in the same manner $$T_{ad,w} = \frac{C_{p,flame} \cdot T_{flame} \cdot M_{flame} + C_{p,o} \cdot T_o \cdot M_o}{C_{p,flame} \cdot M_{flame} + C_{p,o} \cdot M_o}$$

Once again the local specific heats of the two components are determined iteratively with the local gas temperature.

The modelling technique described above is designed to conserve the non-dimensional heat transfer coefficients between the hot standard flame and the cold simulation. The non-dimensional heat transfer coefficient is the Nusselt number which is a function of the scale (d) and the gas conductivity (k) as well as the heat transfer coefficient (h).

$$Nu = \frac{hd}{k}$$

Assuming Nusselt number similarity for the low temperature analogy and the flame condition, the heat transfer coefficients determined in the low temperature tests must be scaled, for use in the numerical simulation at high temperature, by the ratio of the gas conductivities and the inverse ratio of the sizes.

$$h_{flame} = \left(\frac{k_{flame}}{k_{lowtemp}}\right)\left(\frac{D_{lowtemp}}{d_{flame}}\right) h_{lowtemp}$$

This relationship assumes constant gas properties across the boundary layer. In the highly turbulent flow as the plume impinges on the model, heat is transferred across the boundary layer from the hot mixed bulk conditions to the relatively cold wall. The extreme temperature difference between the flow and the wall will result in significant variation of the gas properties across the laminar sublayer. That variation should be accounted for in the scaling of the experimental heat transfer coefficients.

A number of different strategies have been proposed to account for this variation in transport properties of the gas. However, there has only been limited evaluation of these strategies for temperature ratios as low (<0.5), as in the present case. It is therefore required to determine of the most appropriate scaling strategy for the case now under consideration. For the numerical simulation the appropriate corrections should be determined locally and at each time point as the wall temperature will increase during the simulated fire test. This requirement is within the capabilities of known finite element analysis programs as the local heat transfer coefficient can be scaled at each time point as a function of the local metal temperature.

The metal temperatures deduced from the fire tests are also a function of the cooling flow on the rear of the component. While the flow across the rear of the component is essentially a standard duct flow, no accurate correlations exist in the literature for the convection in the cavities on the rear surface. The distribution of surface heat transfer coefficient can however be determined in these regions experimentally.

FIG. 7 illustrates a modification of the set-up of FIG. 5 for measurement in the model of heat transfer coefficient distribution in rear cavities. It will be seen that the heated flow of the gas mixture as before is led through a duct 72 past the face of the model under investigation by means of a pumped suction flow drawn through exhaust conduit 74. Reproduction of the flame plume configuration is not relevant to these tests.

A comparison of the measured levels of h on the wall of the mount ring, away from the cavities, may be made using the correlation of Dittus and Boelter (1930) for fully developed turbulent flow in smooth tubes.

$$Nu_d = 0.023 Re_d^{0.8} Pr^{0.4}$$

where $Re_d$ is based on the hydraulic diameter, and all the fluid properties are determined at the bulk temperature. In the example illustrated here in which the duct upstream of the mount ring is insulated from the flame, the bulk temperature may reasonably be taken as the entry temperature.

Radiative heat transfer can be calculated in the finite element analysis at all external surfaces of the component in the numerical model using an accurate, experimentally determined, value for the emissivity of the metal (as a function of surface temperature). Internal radiation between facing surfaces can also be accounted for in the numerical model.

NOMENCLATURE

A surface area ($m^2$)
$C_p$ specific heat ($J.kg^{-1}.K^{-1}$)
$C_{p,plume}$ specific heat of plume ($J.kg^{-1}.K^{-1}$)
$C_{p,0}$ specific heat of surrounding air ($J.kg^{-1}.K^{-1}$)
d burner head diameter, m
Fr Froude number
g gravitational acceleration ($m.s^{-2}$)
H specific enthalpy ($J.kg^{-1}$)
h local heat transfer coefficient ($W.m^{-2}.K^{-1}$)
$h_c$ heat of combustion ($kJ.kg^{-1}$)
J momentum flux ($kg.m.s^{-2}$)
k gas conductivity ($W.m^{-1}.K^{-1}$)
$L_e$ mean beam length (m)
$L_{e,0}$ mean beam length (m)
M mass fraction
m mass flow rate ($kg.s^{-1}$)
Nu Nusselt number
p partial pressure of gas component (atm)
Pr Prandtl number
$Q_c$ convective heat flux ($W.m^{-2}$)
$Q_r$ radiative heat flux ($W.m^{-2}$)
Re Reynolds number
$r_e$ material resistivity ($\Omega$)
$T_f$ film temperature (K)
$T_g$ gas temperature (K)
$T_i$ initial surface temperature (K)
$T_j$ thermocouple junction temperature (K)
$T_o$ temperature of surroundings (K)
t time since start of heat input (s)
$t_{0.01}$ heat pulse penetration time (s)
u flow velocity ($m.s^{-1}$)
x penetration depth (m)
$\alpha$ thermal diffusivity ($m^2.s^{-1}$)
$\beta$ parameter
$\chi$ radiant fraction
$\epsilon$ emissivity
$\Phi$ equivalence ratio
$\gamma$ ratio of specific heats
$\mu$ dynamic viscosity ($kg.m^{-2}.S^{-1}$)
$\rho$ density ($kg.m^{-3}$)
$\sigma$ Stefan-Boltzman constant

We claim:

1. A method of evaluating the resistance of a component to a fire in which a scale model of the component is provided with a thermochromic liquid crystal on its surface and is subjected to a gas flow at a temperature closer to ambient than to flame temperature, the gas density, flow rate, and the scale of the model being chosen to at least substantially match the Reynolds number and Froude number of the flow over the component in fire test conditions, and to at least substantially match the ratio of flame density to the density of the ambient surrounding in fire test conditions, and the reaction of said liquid crystal is recorded when subjected to the gas flow to permit prediction of the component temperature from heat transfer coefficients of the model derived from said liquid crystal reaction.

2. A method according to claim 1 wherein the gas flow contains at least a substantial proportion of a gas lighter than air.

3. A method according to claim 2 wherein the gas flow contains helium as a major component.

4. A method of simulating a standard flame attack on a component using a scale model of the component having a thermochromic liquid crystal on its surface, in which the scale model is subjected to a gas flow reproducing the plume shape of the standard gas flame but having a substantially lower temperature, the ratio of flame density to density of ambient surroundings being conserved by using a gas comprising helium to give a density substantially lower than that of ambient air, the scale of the model being chosen to at least substantially match the Reynolds number and Froude number of the component in fire test conditions, and the reaction of said liquid crystal being recorded when subjected to the gas flow to permit prediction of the component temperature from heat transfer coefficients of the model derived from said liquid crystal reaction.

5. A method according to claim 4 wherein the heated gas flow is subject to a change of momentum flux which reproduces the ratio of momentum flux of combustion products to total reactant and dilution air momentum flux of the standard gas flame in fire test conditions.

6. A method according to claim 4 wherein the gas flow temperature is less than 90° C.

7. A method according to claim 4 wherein the model test Prandtl number is matched to that of the component in fire test conditions during evaluation of the data obtained from the liquid crystal reaction.

8. A method according to claim 4 wherein the observations under the model test conditions are repeated using liquid crystals having different transition temperatures.

9. A method according to claim 4 wherein the gas flow is led through a duct in which the model is placed for observation of the liquid crystal reaction in regions of the surface shielded from the simulated flame.

10. A flame simulation device for use in low temperature simulation of a standard flame of a fire resistance test, comprising respective sources of pressure air and helium and means for producing a mixed flow therefrom in predetermined proportions and heating said flow, a duct for receiving said flow and simulating a standard test burner, said duct having an exit face formed by a plate with a series of apertures for the passage of the heated mixed gases, said apertures having an area in relation to the area of the duct downstream of the plate which produces a change of momentum flux in said flow substantially reproducing the ratio of the momentum flux of the standard flame combustion products to the momentum flux of the reactants on entry to the standard burner.

11. A heating device according to claim 10 wherein the sources and means for mixing the helium and air are arranged to produce a helium air ratio in the mixture of substantially 96:4.

* * * * *